United States Patent [19]
Liebert et al.

[11] Patent Number: 6,033,731
[45] Date of Patent: Mar. 7, 2000

[54] IMPREGNATING POLYMER BEADS WITH INSECTICIDE

[75] Inventors: Rebecca B. Liebert, Cranberry Township; Christine B. Hetzer, Monaca, both of Pa.

[73] Assignee: Nova Chemicals, Inc., Monaca, Pa.

[21] Appl. No.: 09/136,243

[22] Filed: Aug. 19, 1998

[51] Int. Cl.$^7$ .................................. B05D 5/00; B05D 7/00
[52] U.S. Cl. ........................... 427/244; 427/222; 427/243
[58] Field of Search ..................................... 427/222, 243, 427/244

[56] References Cited

U.S. PATENT DOCUMENTS

| | | | |
|---|---|---|---|
| 4,049,604 | 9/1977 | Morehouse, Jr. et al. | 260/29.6 RW |
| 4,542,162 | 9/1985 | Rutherford et al. | 521/79 |
| 4,994,499 | 2/1991 | Sonnenberg et al. | 521/56 |
| 5,194,323 | 3/1993 | Savoy . | |
| 5,270,108 | 12/1993 | Savoy . | |
| 5,326,777 | 7/1994 | Ludwig et al. | 514/383 |
| 5,704,172 | 1/1998 | Gougeon et al. . | |
| 5,827,522 | 10/1998 | Nowak | 424/405 |

OTHER PUBLICATIONS

Abstract of JP63152648, Date Jun. 25, 1988, Inventor Nobuo Okano, Source—Japan Kokai Tokoyo Koho, 6 pp.
Abstract of JP 10036549, Date Feb. 10, 1998, Inventor: Yoshihiro Toyponaga, Source—Jpn. Kokai Tokkyo Koho, 7 pp.
Abstract of FR 2698632, Date Jun. 3, 1994, Inventor: Jacaues Jean, Source—Fr. Demande, 13 pp.
Abstract of JP 63254143, date Oct. 20, 1988, Inventor—T. Imakita, Y. Tanaka, Source—Jpn. Kokai Tokkyo Koho, 5 pp.
Abstract of Jpn. 63264670, date Nov. 1, 1988, Inventor: H. Mori, M. Mori, Source: Jpn. Kokai Tokkyo Koho, 2 pp.
Abstract of JP 63159451, date Jul. 2, 1988, Inventor: T. Ikeda, Y. Betppu. Source—Jpn. Kokai Tokkyo Koho, 6 pp.

*Primary Examiner*—Shrive Beck
*Assistant Examiner*—Jennifer Calcagni
*Attorney, Agent, or Firm*—Kenneth H. Johnson

[57] ABSTRACT

Polymeric beads made by a suspension or an emulsion process may be concurrently impregnated with blowing agent, an insecticide and a flame retardant, if required. The resulting bead is then washed and dried and then may be used for making a foam structure such as a sheet. The resulting foam sheet may be used in the construction industry, particularly where there is a concern of insect infestation.

8 Claims, No Drawings

IMPREGNATING POLYMER BEADS WITH INSECTICIDE

FIELD OF THE INVENTION

The present invention relates to polymers of vinyl aromatic monomers which contain insecticides. More particularly the present invention relates to foamable or expandable polymers of vinyl aromatic monomers which contain insecticides.

BACKGROUND OF THE INVENTION

Polymeric foam is finding increasing application in the construction industry. However, under some conditions the foam may be subject to insect infestation, and particularly termite infestation. There is a need for methods of rendering polymeric foams resistant to insects.

U.S. Pat. No. 5,194,323 issued Mar. 16, 1993 and U.S. Pat. No. 5,270,108 issued Dec. 14, 1993, both assigned to AFM Corporation, disclose and claim polymeric foams suitable for construction purposes which have been treated with a borate compound to inhibit insect and, particularly, termite infestation. The patent does not teach or suggest that the insecticide could be added to the polymeric beads concurrently with the blowing agent.

U.S. Pat. No. 5,704,172 issued Jan. 6, 1998, assigned to The Dow Chemical Company teaches a rigid polymer foam having a plurality of grooves crossing in diagonal configuration which facilitates the application of insecticides to such rigid foam. The foam may be used for construction purposes. The patent teaches an external post fabrication application of insecticide and does not suggest that the insecticide may be incorporated into the polymer beads concurrently with the blowing agent.

Chemical Abstracts of Japanese Kokai 10036549 A2 published Feb. 10,1998, and Japanese Kokai 63254143 published Oct. 20, 1988 teach applying anti-termite agents to the exterior of foams. The abstracts do not teach or suggest incorporating the insecticides into the polymer beads concurrently with impregnation with the blowing agent.

The Chemical Abstract of French Patent 2698632 published Jun. 3, 1994, teaches the production of very light weight foams, preferably polyurethanes having a density from 5 to 20 g/l. While the patent teaches polyurethanes are preferred, it also teaches that the foam may comprise polystyrene, polyacrylates, and polycarbonates. The disclosure suggests the active substances are preferably introduced into the mixture before polymerization. However, examples 1 and 4 of the patent illustrate the invention using polystyrene foam. The active ingredient is not introduced into the monomer but rather is introduced into "a viscous but liquid styrene prepolymer which has been prepared by heating at 60° C. for an unspecified period of time a mixture of 1000 g of styrene monomer, 1 g of benzoyl peroxide and 70 g of tributyl phosphate as a plastifier". MALATHION is added to the resulting prepolymer. The temperature is adjusted to 45° C. and the mixture is stirred while nitrogen is bubbled through the mixture to obtain a foam having a specific weight of 12 g/l. The patent neither teaches nor suggests that the active ingredient could be incorporated into polymer beads concurrently with impregnation with a blowing agent.

Chemical Abstract of Japanese Kokai 63264670 A2 published Nov. 1, 1988 teaches impregnating polystyrene beads with boron compounds. The abstract of Japanese Kokai 63264670 A2 teaches that beads prepared by a bulk or emulsion polymerization are wetted with water and impregnated with boric acid. The abstract does not teach or suggest that the polymeric beads could be concurrently impregnated with blowing agent and insecticide.

Chemical Abstract of Japanese Kokai 63159451 A2 published Jul. 2, 1988 teaches impregnating polystyrene beads with compounds selected from the group consisting of Phoixom, Fenitrothion, Cyanophos, Acephate and Prothiophos, concurrently with impregnation with a blowing agent. However, the active ingredients do not appear to be soluble in the blowing agent as the impregnation takes place using a solvent or an auxiliary solvent for the active ingredient together with the blowing agent. The present invention has eliminated the solvent or auxiliary solvent which is necessary in accordance with the Japanese Kokai.

Chemical Abstract of Japanese Kokai 63152648 teaches impregnating an expandable polystyrene bead with 2 ppm of Chloropyrifos. This teaches away from the present invention as the bead is an expandable bead (i.e. already impregnated with blowing agent). Further the amount of insecticide is less than that of the present invention.

None of the above art discloses concurrently impregnating polymeric beads with blowing agent and an insecticide in the absence of a solvent.

SUMMARY OF THE INVENTION

Accordingly, one aspect of the present invention provides a process for incorporating an insecticide into an expandable bead of a thermoplastic polymer comprising impregnating said bead with from 100 to 10,000 ppm of said insecticide based on the weight of the thermoplastic concurrently with the impregnation of said bead with from 1 to 10 weight % based on the weight of said polymer of a blowing agent selected from the group consisting of $C_{4-6}$ alkanes.

Preferably the process of the present invention is carried out in the absence of any additional solvent or auxiliary solvent for the insecticide.

BEST MODE

The thermoplastic of the present invention may comprise from 100 to 60 weight %, preferably from 100 to 80 weight % of one or more $C_{8-12}$ vinyl aromatic monomers and up to 40 weight %, preferably not more than 20 weight %, of other ethylenically unsaturated copolymerizable monomers. Examples of suitable vinyl aromatic monomers include, but are not limited to, styrene, alpha-methyl styrene, aromatic $C_{1-4}$ alkyl substituted styrenes such as p-methyl styrene, p-ethyl styrene, p-isopropyl styrene, p-tert-butyl styrene and the like. Other ethylenically unsaturated copolymerizable monomers may also be used including, for example, acrylic acid, methacrylic acid, maleic anhydride, methyl methacrylate, methyl acrylate, ethyl acrylate, butyl acrylate, acrylonitrile, methacrylonitrile and the like.

A particularly useful thermoplastic is polystyrene in which the monomer is 100% styrene.

The insecticide may be incorporated into beads of the polymer in an amount from 100 to 10,000 parts per million (ppm) (corresponding to from 0.01 to 1 weight %), preferably from 300 to 5,000 ppm (corresponding to from 0.03 to 0.5 weight %), based on the weight of the polymer.

While a number of insecticides are available, some useful insecticides may be selected from the group consisting of 1-[(6-chloro-3pyridinyl)methyl]-4,5-dihydro-N-nitro-1H-imidazol-2-amine and 3-(2,2-dichloroethenyl)-2,2-dimethylcyclopropanecarboxylic acid cyano(3- phenoxyphenyl)-methyl ester (cypermethrin), the active ingredient in, for example, Demon TC sold by Zeneca; 3-(2,2dichloroethenyl)-2,2-dimethylcyclopropanecarboxylic acid (3-phenoxyphenyl) methyl ester (permethrin), the active ingredient in, for example, Dragnet FT and Torpedo sold by Zeneca; and 1-[(6-chloro-3-pyridinyl)methyl]-4,5-dihydro-N-nirto-1H-imidazol-2-amine (imidacloprid) the active ingredient in, for example, Premise sold by Bayer. The insecticide should be transported into the polymer bead together with the blowing agent. Preferably the insecticide should be at least moderately soluble in the blowing agent.

The thermoplastic beads of the present invention may be polymerized in a conventional suspension or emulsion polymerization. Generally, thermoplastics comprising a major amount of a vinyl aromatic monomer and a minor amount of one or more copolymerizable monomers may be polymerized using a thermal and/or free radical initiation. The monomer(s) is/are suspended or dispersed in a different, non-hydrocarbon, typically aqueous, phase and the polymerization takes place in the dispersed monomer droplets (e.g. suspension) or in a micelle into which monomer diffuses from the monomer droplets (e.g. emulsion).

The monomers are suspended in water from about 50 to 500 parts (preferably, about 75 to 250 parts) by weight per 100 parts by weight of the monomers using an effective amount of one or more suitable suspending agents. Any of the suspending agents useful in the suspension polymerization of vinyl aromatic polymers may be used. Examples of suitable suspending agents include finely divided water insoluble inorganic substances such as tricalcium phosphate, and the like as well as water-soluble polymers such as polyvinyl alcohol, alkyl aryl sulfonates, hydroxyethyl cellulose, polyacrylic acid, methyl cellulose, polyvinyl pyrrolidone, and low molecular weight (preferably having an Ms less than about 5,000 polyalkylene glycols (e.g. polyethylene glycols and polypropylene glycols) and the like. Auxiliary suspending agents such as sodium linear alkylbenzene sulfonates may also be employed. The use of tricalcium phosphate together with a sodium linear alkylbenzene sulfonate is particularly useful. The amount of the suspending agent necessary will vary depending on a number of factors but will generally be from about 0.01 to 1 part by weight per 100 parts by weight of the vinyl aromatic polymer. One or more surfactants such as a polyoxyalkylene derivative of sorbitan monolaurate or other fatty acid ester, an ethylene oxide/propylene oxide block copolymer, or other non-ionic or anionic surface active agent can be added to the aqueous suspension if desired. The preferred amount of surfactant is from about 0.01 to 1 part by weight per 100 parts by weight of monomer.

In addition to the monomers, the aqueous suspension may further include a free radical initiator or free radical initiator system. The free radical generator may be a peroxide such as hydrogen peroxide or benzoyl peroxide, or a persulfate initiator.

The reaction mixture is heated to initiate polymerization, either thermally or by a free radical catalyst. After the monomers are polymerized to form particles or beads (generally resulting from the suspension process) or microparticles (generally resulting from the emulsion process), they may be separated from the aqueous phase and washed. The thermoplastic polymer beads are typically from about 0.1 to 2 mm in average diameter.

Generally, the polymer bead is impregnated with a blowing agent to make expandable thermoplastic beads (polystyrene). Typically the beads may be impregnated with from 1 to 10 weight %, preferably from about 3 to 8 weight %, based on the weight of the polymer of one or more blowing agents selected from the group consisting of $C_{4-6}$ alkanes. Typical blowing agents include butane, pentane and hexane. While the CFC's and HCFC's such as dichlorodifluoromethane, trichlorofluoromethane and dichlorofluoromethane have some suitable properties as blowing agents, their use is not recommended.

In the suspension process the polymer beads may be impregnated either concurrently with the later part of the polymerization or after polymerization. In the impregnation process the blowing agent, together with the insecticide, are added to an aqueous suspension containing polymeric beads. The suspensions, together with the blowing agent and the insecticide, are maintained at a temperature typically from about 60° C. to 110° C. for a period of time from about 2 to 4 hours by which time the blowing agent and insecticide have impregnated the polymeric beads. The beads are then separated from the emulsion, optionally washed and dried.

The resulting beads are stored preferably in a cool dark environment. When used to produce a foam product, typically the beads are first partially expanded and then placed in a mold and fully expanded resulting in a fusion of the foamed beads and a closed cell foam. Generally, for construction industry purposes, the foam will take the form of a sheet.

The present invention will now be illustrated by the following examples. In the examples unless otherwise indicated, parts means parts by weight (e.g. grams) and per cent means weight per cent.

In a preferred embodiment of the present invention the polymer may further incorporate a flame retardant. Typically the flame retardant is incorporated into the polymer in an amount from 5,000 ppm to 50,000 ppm (0.5 weight % to 5 weight %), preferably from 7,500 ppm to 15,000 ppm. In the suspension or emulsion process the flame retardant may be added to the monomer or aqueous phase, depending on solubility in the monomer/polymer. In the bulk process and, optionally, in the suspension and emulsion process, the flame retardant may be added to the resulting polymer by coating it or adding it as part of an additive package in an extrusion process. Suitable flame retardants are known to those skilled in the art. Some flame retardants include hexabromocyclododecane, dibromoethyldibromocyclohexane, tetrabromocyclooctane, tribromophenol alkyl ether, tetrabromobisphenol A—bis (2,3-dibromopropyl ether).

EXAMPLE 1

Styrene monomer was suspended in an aqueous phase in the presence of 0.20 weight % of a primary inorganic suspending agent and 0.25 weight % of a secondary anionic surfactant suspending agent, based on the weight of the styrene monomer. Low and high temperature peroxide initiators were added at levels of 0.34 and 0.066 weight %, respectively. Nucleation agents were also added at levels of 0.2 weight %. The resulting suspension was heated to 90° C. and the first phase of the polymerization of styrene monomer to polymer was carried out over 5.5 hours. The suspension was then heated from 90–115° C. and the second phase of the polymerization was carried out over 2 hours. The resulting beads were washed, dried and re-suspended in water with 0.6 weight % primary suspending agent. Imidacloprid was added to the suspension at 0.03 weight % based on the weight of the polymer in the absence of any additional solvent for the imidacloprid. The suspension was heated from 70–115° C. over 2.5 hours as 7.2 weight % of pentane was added to the system. The system was held at 115° C. for 1.5 hours to fully impregnate the polystyrene beads with the blowing agent and the imidacloprid. The resulting beads were then washed, dried and lubed with 0.15 weight % stearate.

The resulting beads were then partially expanded in steam. After aging, the pre-expanded beads were placed in a closed mold and heated to 115° C. to fully expand and fuse them together. The result is a sheet or shape of foam. No negative performance characteristics were observed in the blowing of the foam.

It should be noted that the insecticide imparted a light brown tint to the impregnated beads.

Experiment 2

The procedure of experiment 1 was repeated, except that the amount of imidacloprid was 0.3 weight % based on the weight of the polymer. The polymer was again tinted a light brown. Again there was no negative performance characteristics observed in foaming the beads.

Experiment 3

The procedure of experiment 1 was repeated except that cypermethrin was used at a level of 0.3 weight % based on the weight of the polymer. Again there were no negative performance characteristics observed in foaming the beads.

What is claimed is:

1. A process for incorporating from 100 to 10,000 ppm based on the weight of thermoplastic of an insecticide selected from the group consisting of 1-[(6-chloro-3-pyridinyl)methyl]-4,5-dihydro-N-nitro-1H-imidazol-2-amine; 3-(2,2-dichloroethenyl)-2,2-dimethylcyclopropanecarboxylic acid cyano-(3-phenoxyphenyl)-methyl ester; and 3-(2,2-dichloroethenyl)-2,2-dimethylcyclopropanecarboxylic acid (3-phenoxyphenyl)-methyl ester into an expandable bead of a thermoplastic polymer prepared by suspension or emulsion polymerization of a monomer mixture consisting of 100 to 60 weight % of one or more monomers selected from the group consisting of styrene, alphamethyl styrene and p-methyl styrene and from 0 to 40 weight % of a monomer selected from the group consisting of acrylic acid, methacrylic acid, maleic anhydride, methyl methacrylate, methyl acrylate and ethyl acrylate, comprising concurrently impregnating said bead with said insecticide and from 1 to 10 weight % based on the weight of said thermoplastic of one or more blowing agents selected from the group consisting of butane, pentane and hexane.

2. The process according to claim 1, wherein said one or more monomers mixture is 100 weight % of styrene.

3. The process according to claim 2, wherein said insecticide is incorporated into said thermoplastic in an amount from 300 to 5,000 ppm based on the weight of thermoplastic.

4. The process according to claim 3, further comprising adding from 5,000 to 30,000 ppm based on the weight of said thermoplastic of a flame retardant selected from the group consisting of hexabromocyclododecane, dibromoethyldibromocyclohexane, tetrabromocyclooctane, tribromophenol allyl ether, tetrabromobisphenol A—bis (2,3-dibromopropyl ether).

5. The process according to claim 4, wherein said thermoplastic is prepared by a suspension process.

6. The process according to claim 5, wherein said insecticide is 1-[(6-chloro-3-pyridinyl)methyl]-4, 5-dihydro-N-nitro-1H-imidazol-2-amine.

7. The process according to claim 5, wherein said insecticide is 3-(2,2-dichloroethenyl)-2,2-dimethylcyclopropanecarboxylic acid cyano(3-phenoxyphenyl)-methyl ester.

8. The process according to claim 5, wherein said insecticide is 3-(2,2-dichloroethenyl)-2,2-dimethylcyclopropanecarboxylic acid (3-phenoxyphenyl)-methyl ester.

* * * * *